(12) United States Patent  (10) Patent No.: US 8,771,213 B2
Wens  (45) Date of Patent: Jul. 8, 2014

(54) ORTHOPEDIC FOOT SUPPORT

(75) Inventor: Heidi Jeanne Victor Wens, Merksplas (BE)

(73) Assignee: Theweco BVBA, Merksplas (BE)

( * ) Notice: Subject to any disclaimer, the term of this patent is extended or adjusted under 35 U.S.C. 154(b) by 47 days.

(21) Appl. No.: 13/636,161

(22) PCT Filed: Mar. 21, 2011

(86) PCT No.: PCT/BE2011/000014
§ 371 (c)(1),
(2), (4) Date: Sep. 20, 2012

(87) PCT Pub. No.: WO2011/116435
PCT Pub. Date: Sep. 29, 2011

(65) Prior Publication Data
US 2013/0012854 A1    Jan. 10, 2013

(51) Int. Cl.
*A61F 5/00*    (2006.01)

(52) U.S. Cl.
USPC ............... 602/23; 602/26; 602/27; 128/882

(58) Field of Classification Search
USPC ............... 128/845, 882; 602/23, 32, 26, 27; 5/625, 636
See application file for complete search history.

(56) References Cited

U.S. PATENT DOCUMENTS

| | | | |
|---|---|---|---|
| 2,911,657 A | 11/1959 | Streter, III | |
| 3,511,233 A | 5/1970 | Holy, Jr. | |
| 3,783,863 A * | 1/1974 | Kliever | 128/847 |
| 5,101,526 A * | 4/1992 | Smith | 5/630 |
| 5,603,336 A * | 2/1997 | Shepich | 128/882 |
| 5,725,486 A | 3/1998 | Engelman | |
| 6,000,399 A * | 12/1999 | Choy | 128/845 |
| 2005/0060808 A1 | 3/2005 | Shaw | |

FOREIGN PATENT DOCUMENTS

CH    447 474    11/1967

OTHER PUBLICATIONS

International Search Report dated Aug. 24, 2011, corresponding to PCT/BE2011/000014.

* cited by examiner

*Primary Examiner* — Michael A. Brown
(74) *Attorney, Agent, or Firm* — Young & Thompson

(57) ABSTRACT

Orthopaedic foot support (1) to support long-term bedridden patients, characterized in that the foot support includes a preformed support of two parts, i.e. a top piece (2) that consists of a stiff cushion (3) with an erect wall (4) and transverse supports (5,6,7) connected to it for the lateral support of the lower legs (16), and a bottom piece that consists of a base (8) on which the lower legs can rest and whereby the base (8) has a pair of cambers (10) to support the lower legs (16), and whereby the base (8) can be exchanged by a base with different cambers (10) suitable for another leg dimension, and whereby the top piece (2) can be removed to gain access to the legs of the patient who remains lying on the base (8), without having to move this base (8) or the legs (16).

27 Claims, 6 Drawing Sheets

ORTHOPEDIC FOOT SUPPORT

The present invention relates to an orthopaedic foot support to support bedridden patients, in other words who have to spend a considerable time in bed.

More specifically, the invention is intended to support the heels and/or lower legs and feet of patients who have to spend a long time lying in bed.

Such patients are for example people with permanent paralysis of the legs, bedridden elderly people, patients who wear orthoses but who must keep their feet and lower legs in position when the orthoses are removed, patients who present an increased risk of decubitus in the heels, etc.

It is known that with long term patients, coma patients and patients with temporary paralysis, it is important that the feet are kept in the right position while bedridden in order to prevent medical complications.

These complications can go from bedsores to a shortening of the Achilles tendon with the resulting clubfoot formation. By lying in bed for a long time, patients tend to keep their feet towards the bed end in line with the lower legs, such that when this position of the feet is maintained for a long time the Achilles tendon can shorten.

This phenomenon is known by the name of the resulting clubfoot, and has to be avoided as much as possible as this will unnecessarily lengthen the recovery period of the patient.

The heel in particular is susceptible to the complication of bedsores or decubitus, as the heel absorbs the pressure of the feet and everything resting on the feet, such as the bed covers.

A conventional method for preventing complications in the feet as a result of being bedridden is the application of physiotherapy. However this form of treatment is labour intensive and must be maintained with an adequate frequency, without being able to ensure a permanent correction of the position of the feet.

This of course brings about extra costs for the patient or for the health insurance.

Traditionally people have attempted to avoid such complications by placing a separate cushion behind the feet of the patient in bed.

A disadvantage of such a separate cushion is that it provides inadequate support for the feet and has to be put back in the right position a number of times per day and night by the nursing staff, which means additional work pressure on the already highly loaded nursing staff.

Another disadvantage is that the cushion does not provide any support for the heel, which in this position is vulnerable to bedsores.

A further disadvantage is that pressure is exerted on the feet by the bed covers resting on the feet, and which are required to keep the feet warm.

Another known method for preventing these complications is to regularly place the patient for some time in a suitable brace that secures the lower leg and foot, but which has the disadvantage that it has to be made to measure out of hard plastic or metal, whereby a suitable brace is not immediately available to the patient.

This means that while such a brace is being made to measure, a certain form of clubfoot formation can already occur, as it can occur after a relatively short period of one to two weeks.

A further disadvantage of such a brace is that it is not comfortable for the patient due to its hard surface, and with long term use it can also give rise to bedsores.

A further disadvantage is that such a brace cannot be permanently worn and the nursing staff have to put it on and take it off.

In order to absorb the pressure of the bed covers on the feet, the use of a plastic or metal arch is known that is placed over the feet so that the bed covers are supported by it.

A disadvantage of such an arch is that the arch does not prevent the feet being put in an undesired position.

A further disadvantage of such an arch is that it hampers keeping the feet warm, because there is no contact between the bed covers and the lower legs and/or feet.

In order to avoid bedsores on the heels, the current means are insufficient.

Ring cushions or shapes with a circular recess move the pressure to the vicinity of the ring and increase the pressure there. In the centre of the ring the tissue can even become ischaemic.

Generally it is chosen to place a separate cushion under the lower legs. This cushion must be positioned correctly otherwise it loads the knee joint. The cushion can move and then it always has to be corrected by the carer.

In order to position the feet correctly and to prevent bedsores on the heels, two cushions are put at the foot end. This is in combination with the cover arch. However, this situation is not practical to the carer.

CH 447.474 describes a leg support intended to support injured patients during transport after an accident, for example.

This leg support can support the entire leg of the injured person and consists of a main part with recesses for supporting the legs of the patient, which are open along the top and presents a foot support at the foot end that can keep the foot upright.

A disadvantage of this leg support is that it is not suitable for treating long term bedridden patients, because the sidelong support of the legs cannot be removed without moving the legs, which thus hampers the care of the legs and the maintenance of the cushion.

A further disadvantage of this leg support is that the foot support does not stay upright by itself but has to be supported by a frame against which it is secured.

An additional disadvantage is that this leg support does not enable the patient to temporarily adopt a sideways lying position, because the supporting element between the two legs cannot be removed.

A further disadvantage of this leg support is that it is not suitable for preventing bedsores, because the heel is not kept in a floating position and the materials in contact with the legs are not designed to prevent bedsores, but to prevent the displacement of fractures due to transport.

A further disadvantage is that this leg support cannot be adjusted optimally to the physiognomy of the patient. An insert on the sole adjusts the leg length to the actual leg length, which does not change or adjust the rest of the leg support and which provides no suitable support of the lower leg.

U.S. Pat. No. 2,911,657 describes a foot support that ensures that the heels are supported in a "floating" position, i.e. the heels have no contact with the foot support such that bedsores on the heals are avoided.

The disadvantage of this foot support is that it does not provide any sideways support for the lower leg, but on the contrary allows lateral movement, so that the feet can tilt sideways. When bedridden for a long time, the muscles stiffen and the ankle joint in this position is called varus tilting. This complication brings about a painful extension of the recovery period.

This is particularly important with long term bedridden patients during the repair of a hip fracture, whereby the legs are in a straddle position and the feet can tilt very easily if they are not supported laterally.

The purpose of the present invention is to provide a solution to the aforementioned disadvantages and other disadvantages.

To this end, the invention concerns an orthopaedic foot support to support bedridden patients, consisting of a preformed support of two parts, i.e. a top piece that consists of a stiff cushion with an erect wall and transverse supports connected to it for the lateral support of the lower legs, and a bottom piece that consists of a base on which the lower legs can rest and whereby the base has a pair of cambers to support the lower legs, and whereby the base can be exchanged by a base with different cambers suitable for another leg dimension, and whereby the top piece can be removed to gain access to the legs of the patient who remains lying on the base, without having to move this base or the legs, and whereby the base and the erect wall of the top piece form a right angle or practically form a right angle so that the feet form a right angle or practically form a right angle with respect to the lower leg.

In a preferred embodiment, between the cambers to support the lower leg and the upright wall of the top piece, there is a hollow in the base such that the heel floats above the underlying base.

An advantage of such a foot support is that complications are prevented, ranging from bedsores to a shortening of the Achilles tendon with the formation of clubfoot.

A further advantage of this foot support is that it can provide permanent support for the bedridden patient, without labour intensive interventions by the nursing staff.

Another advantage is that the recovery period of the bedridden patient is substantially reduced and the need for physiotherapy treatment can be limited or avoided.

Indeed, it is possible to provide a few preformed bases with cambers of different dimensions, from which a suitable size for the patient concerned can be chosen. As a result a relatively long waiting time is avoided for making a foot support to size, whereby the foot and the leg are fixed in the right position right from the start.

A further advantage is the increased comfort for the bedridden patient, who experiences no further pressure from the bedcovers on his feet, and is confident that his feet are kept in the right position, without the patient always having to worry about keeping his feet in the right position, or even with a comatose patient who cannot concern himself with such a thing.

A further advantage is that both legs can be supported at the same time, whereby the legs lie in a natural position with a slight or broader straddle position for a hip fracture or abduction cushion after a hip operation, and whereby the legs cannot be placed over one another. The legs lie symmetrically, starting from a correct foot position, whereby the patient cannot turn his feet outwards, cannot turn on his side or lift or cross his legs, such that the feet are fixed in a square position with respect to the lower leg, which prevents the Achilles tendon shortening due to lying in bed for a long time and it keeps the pressure off the heels.

This positioning of the legs is also important, for example for the repair of a pelvis fracture or pelvis operation, whereby it is necessary to stabilise the legs in the right position while the fracture or wounds are healing.

An advantage of the foot support is that the feet are correctly positioned, and the use of sandbags against the legs or Velcro strips on the feet to keep them in the right position is no longer necessary.

The use of a large triangular shape that is placed between the legs is superfluous because the foot support takes over this function.

Also the use of leg channels, in the form of a half tube is superfluous here, and thus also the uncomfortable dangling of the feet after the channel and the uncomfortable feeling of the hard, hollow surface that does not fit the physiognomy of the legs.

The use of a leg channel with foot support and a ring-shaped recess for the heel is avoided, along with the resulting oedema formation and bedsores on the edge of the recess.

If necessary a band can be placed around the cushion at the level of the lower leg, whereby the band can be secured with a buckle for example.

Preferably the top piece of the foot support can be released from the base in order to remove it, and it can be secured again after it has been put back on the base.

An advantage attached to this is that the nursing staff can remove the top piece of the foot support in order to gain access to the legs of the patient without having to move them and while these legs continue resting on the base of the foot support.

This makes the care of the patient easier for the nursing staff and less inconvenient for the patient.

In a preferred embodiment the top piece is hinged to the base so that the top piece can easily be turned upwards to release the legs.

This not only facilitates the care of the patient but also the maintenance of the orthopaedic foot support itself, due to all surfaces being readily accessible for the cleaning or disinfection of them.

Preferably the top piece can be secured to the base by means of buckles or telescopic parts that fit together to enable both components to be joined together or separated depending on the requirement.

Preferably the pair of cambers on the base of the foot cushion are made from a material that automatically takes on the shape of the lower leg of the patient, such as a viscoelastic foam or gel pad.

These materials, such as Tempur® for example, have the advantage that the patient feels that his supported body part is weightless due to the automatic spread of the load.

Preferably the bottom edge closest to the back of the knee of the patient is located at a height between 1 and 3 cm and this in order not to load the knee joint.

For a bedridden patient a foot support is just as important as a pillow. The shape enables the transition from the bed to the foot support to be a very low height of 1 to 3 cm in soft foam, so that the patient does not feel the transition just behind the back of the knee and can adopt a naturally stretched position without loading the knee joint.

Preferably the area of the base of the foot cushion is no greater than the movable surface of a positionable hospital bed on which the lower legs rest.

An advantage of this dimension is that the bed can be repositioned without impeding the support of the lower legs and feet.

Preferably the central transverse support, which keeps the two legs separated can be removed, in order to enable a temporary sideways position for the patient.

This can be realised by providing a centre piece that can be slid out and removed and then slid back depending on the requirement.

Preferably the surface of the base and/or the top piece is covered with an anti-slip material. Such a covering prevents the cushion sliding off if the support surface on which it rests is sloping.

Preferably the top piece and/or the base of the orthopaedic foot support is made from a hard foam, such as polyether or polyurethane, or a medical cold foam that meets the medical requirements.

The shape of the foot support can be obtained by contour cutting and can consist of a mix of different foam types, perhaps of different densities, whereby it is ensured that the foam has a good breathing properties.

An advantage of the shape is that the foot support enables bedsores to be prevented, even in a semi-fowler position and this in a very soft comfortable way for the patient.

Preferably the foam used is of a fire-retardant or fire-resistant type, and it is an antibacterial and/or antiviral medical foam.

The form can be finished with a coating or an elastic polyurethane skin that can be disinfected with surface cleaning.

Preferably the core of the foot support of hard foam is covered with a softer material to improve the lying comfort of the patient.

This can be in the form of a liner that is secured to the shape by means of stitching. The seams of the liner can be stitched or welded.

The liner is preferably manufactured with breathing properties so that transpirational fluid can be removed or penetrating liquids due to incontinence can be evacuated.

Thus the foot support can be covered or consist of a material that has properties to prevent bedsores, such as the MEDITISSE®PRO material or other commercial materials of producers such as FOAM FOR CARE.

The foot support can also be covered or consist of a material that has antibacterial, antiviral and/or antifungal properties.

Preferably the foot support is covered with or manufactured from a material that can be washed or sterilised at 95° C. in an automatic wash or by surface cleaning with disinfectant products to which the material is resistant.

An advantage of this covering is that the support feels soft for the patient in all places, and if desired this covering can also be changed.

Preferably the cambers in the base are formed by inserts chosen from a series of preformed inserts, according to the physiognomy of the lower leg and foot of the patient.

An advantage of such an insert is that it can be adapted to the shape and dimensions of the lower legs and feet of the patient concerned.

Preferably the cambers in the base are formed by inserts chosen from a series of preformed inserts, according to the physiognomy of the lower leg and foot of the patient.

An advantage of such an insert is that it can be adapted to the shape and dimensions of the lower legs and feet of the patient concerned.

It goes without saying that the cambers in the base can also form part of the base, and can be replaced with the base by cambers of a different size or shape, adapted to the physiognomy of the patient.

Preferably the top piece and/or base have securing means to secure them in place at the foot end of the bed.

An advantage of such a shape of the foot support is that the support remains in the desired position without the intervention of the nursing staff, and that the support cannot be involuntarily moved by the patient, for example while sleeping.

Preferably the height of the stiff upright cushion of the top piece is such that the patient can at most stick his toes above the stiff upright cushion.

An advantage of such a form of the foot support is that the patient is no longer bothered by the pressure of the bed covers, which can detrimentally influence the position of the feet and the comfort of the patient.

If the foot support is not higher than the feet of the patient, one or more end pieces can always be provided that ensure that the bed cover over the foot support does not come into contact with the feet of the patient.

A further advantage of such a form is that the feet are kept warm by the bed cover, because the bed cover can fit around the foot support.

If required, a band can be attached at the level of the lower legs around the base and the top piece of the foot cushion. This is in order to ensure the supporting action of the foot cushion, for example while asleep.

If required, the central transverse support of the top piece can be constructed so that a straddle position of both legs is ensured, whereby the two other supports are side supports on either side of the legs.

Preferably the transverse supports slope down obliquely in their longitudinal direction from the upright cushion to the edge of the base that is the closest to the backs of the knees, and this in order to keep the upper legs warm with the bed covers.

With the intention of better showing the characteristics of the invention, a preferred embodiment of an orthopaedic foot support according to the invention is described hereinafter by way of an example, without any limiting nature, with reference to the accompanying drawings, wherein:

FIG. 1 schematically shows in perspective an orthopaedic foot support according to the invention in a closed state.

Figure 1:
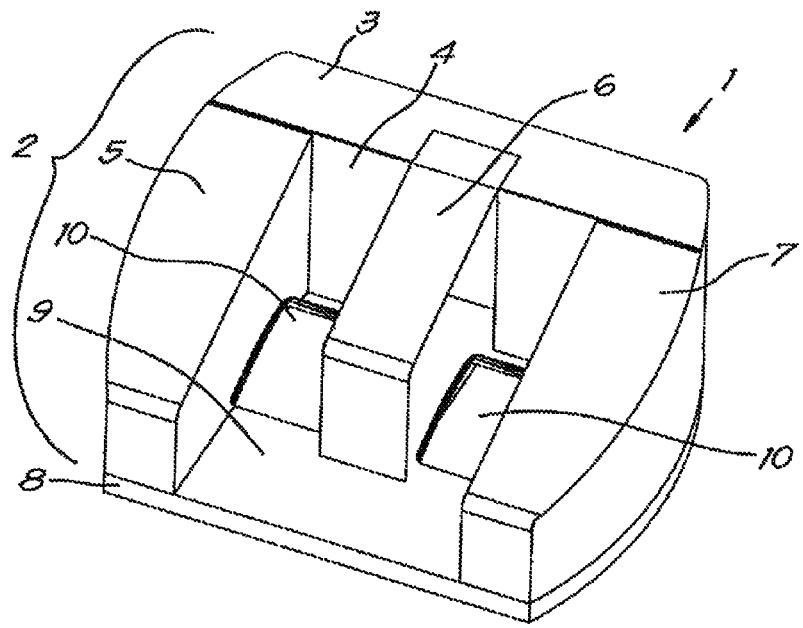

FIG. 1 presents the orthopaedic foot support 1 according to the invention that comprises a top piece 2 that consists of a stiff cushion 3 with an upright wall 4 and to which are connected transverse supports (5, 6, 7) for the lateral support of the lower legs, and a bottom piece 8 that consists of a base 9, with a pair of cambers 10 that form part of inserts that are placed in the base 9 or which form part of the base 9 itself.

Figure 2:
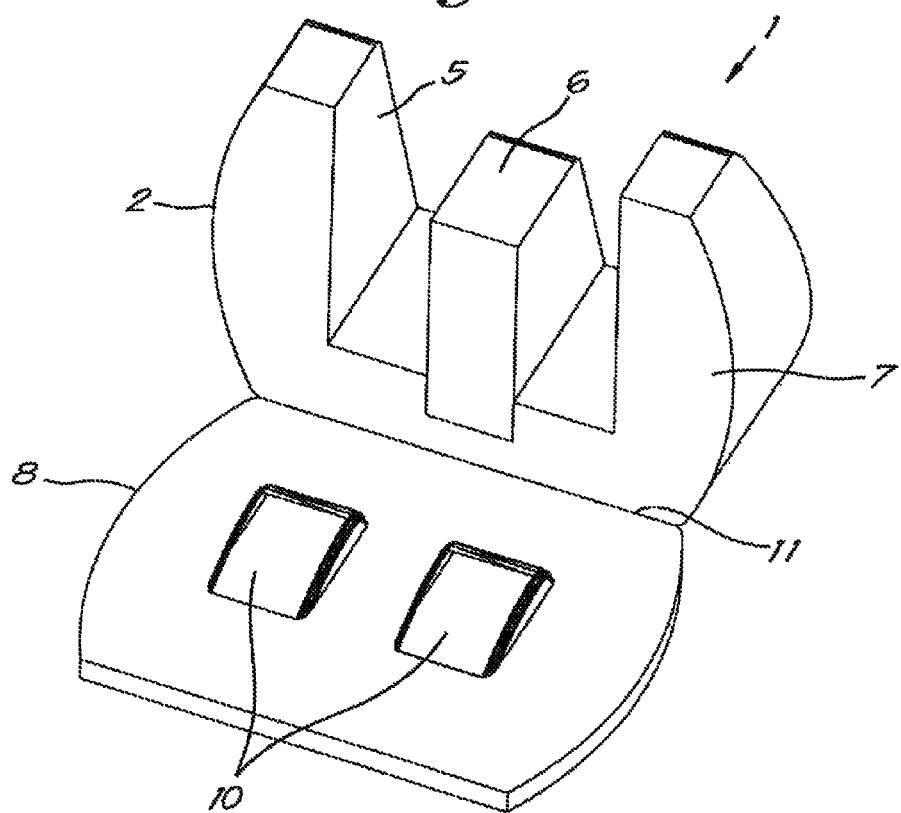
FIG. 2 shows FIG. 1 in an open state.

FIG. 2 presents the same orthopaedic foot support 1, but now in an open state, whereby the top piece 2 is turned upwards around a hinged side 11, with which the top piece 2 and the base 8 are attached to one another.

Figure 3:
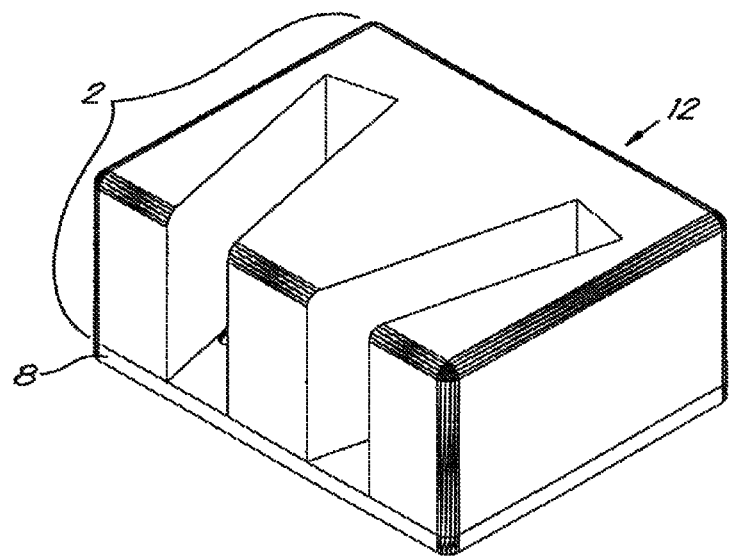
FIG. 3 shows an alternative embodiment of the invention in a closed state.

FIG. 3 presents an alternative embodiment 12 of the invention that is suitable for supporting legs in a straddle position, and this in a closed state whereby the top piece 2 rests on the base 8.

Figure 4:
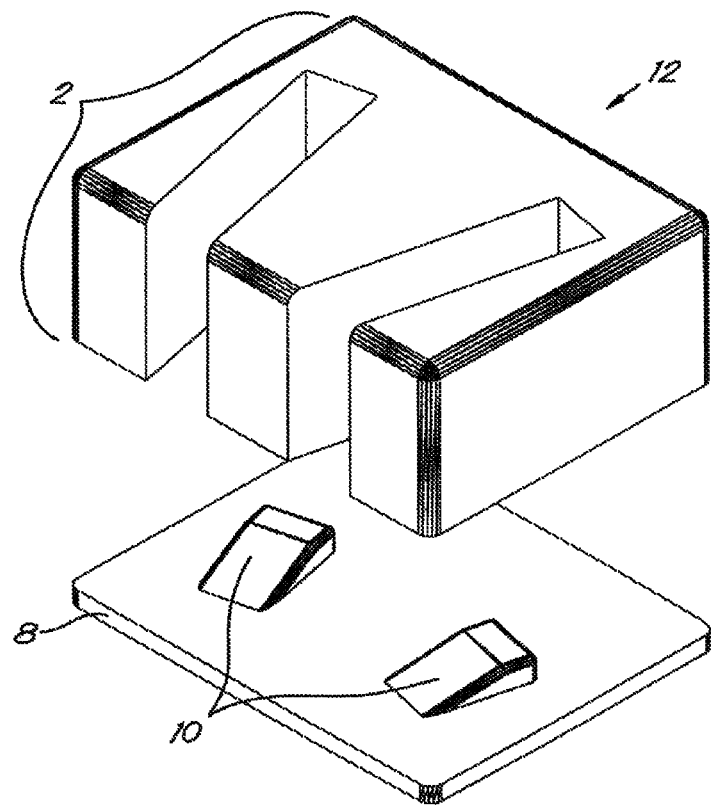
FIG. 4 shows FIG. 3 but in an open state.

FIG. 4 presents the same alternative embodiment 12, but now in an open state, whereby the top piece 2 and the base 8 are not attached together and whereby the top piece 2 is removed from the base 8.

Figure 5:
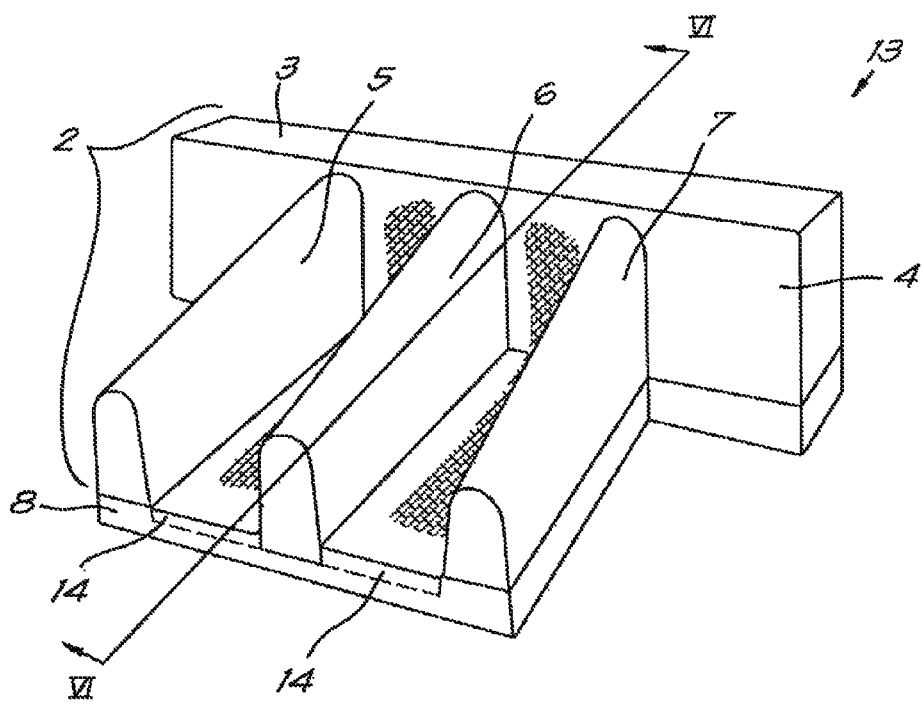
FIG. 5 shows an alternative embodiment of the invention.

FIG. 5 presents a variant 13 of the invention, whereby the base piece 8 has inserts 14 that have cambers 10 and whereby the central transverse support 6 can be removed.

Figure 6:
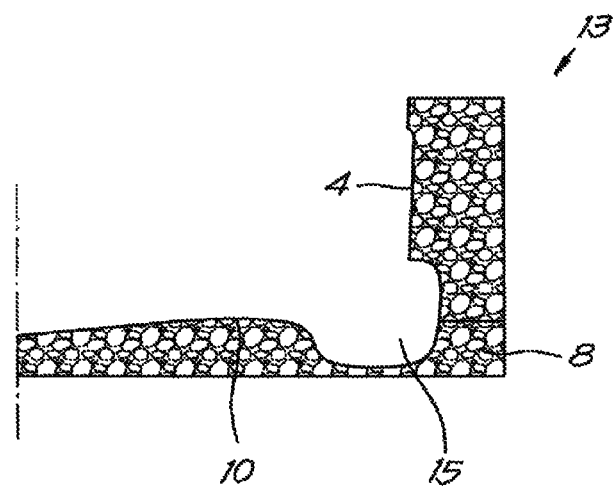
FIG. 6 shows a cross-section according to line VI-VI of FIG. 5.

As shown in FIG. 6, the sole is supported by the upright wall 4 whereby the base 8 and the upright wall 4 form a right angle or practically form a right angle. Between the upright wall 4 and the camber 10 to support the lower leg there is a hollow 15 that ensures that the heel is supported floating and does not make contact with the foot support 13.

Figure 7:
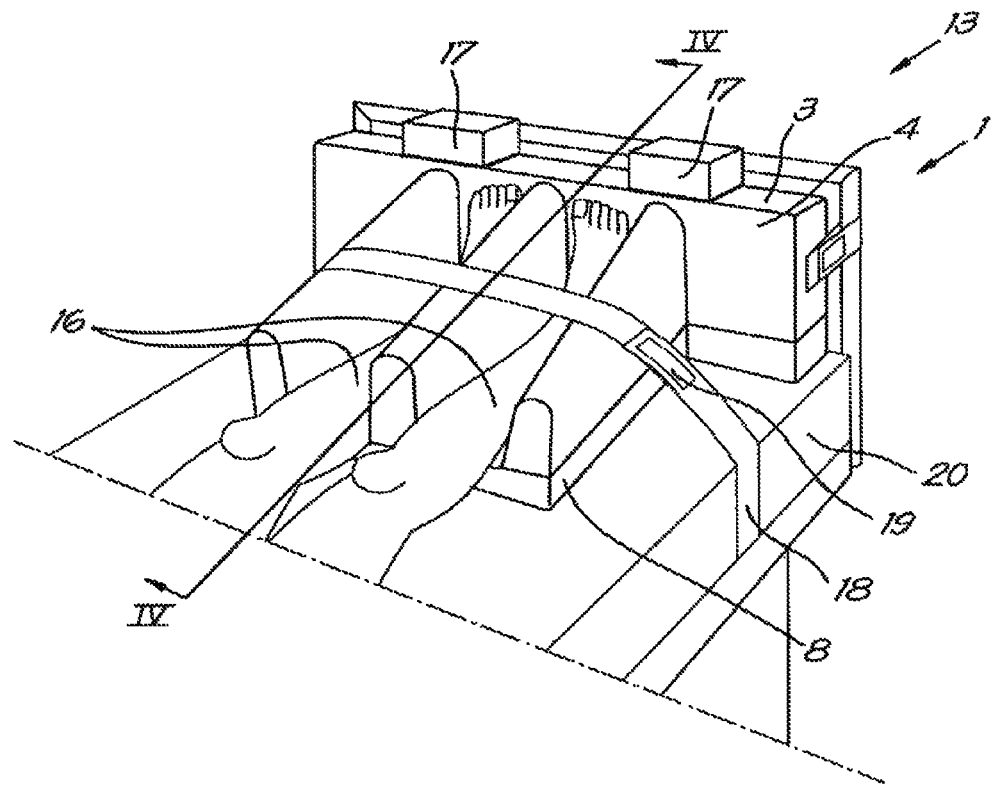
FIG. 7 shows the use of FIG. 5 in perspective.

FIG. 7 illustrates the use of the foot support 13, whereby the legs 16 of the patient lie in the foot support 13. The beam shaped cushion 3 can have securing means to attach it to the foot end of the bed, in this case in the form of belts with a fastener.

The beam shaped cushion 4 can also have extension pieces 17 to make it higher than the foot of the patient, in this case blocks 17 secured with an attachment to the block shaped cushion 2.

At the level of the lower legs 16, a band can be placed around the foot support, which for example is secured to the bed 20 by means of an attachment 19.

Figure 8:
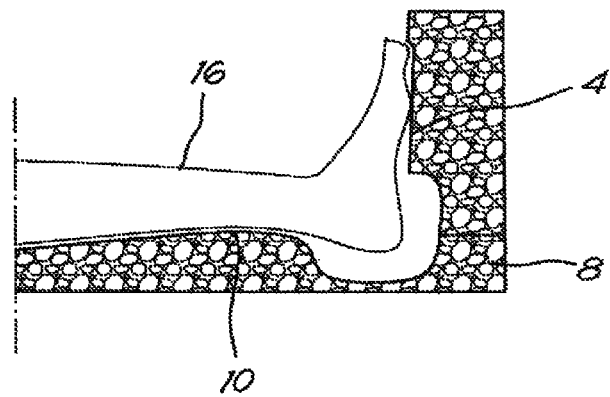
FIG. 8 shows a cross-section according to line VI-VI of FIG. 6 with a lower leg and foot.

The camber 10 of the base 8 and the upright wall 4 of the foot support ensure that the position of the feet is always upright with respect to the bed and forms a right angle or practically forms a right angle to the position of the lower leg 16 as long as the patient is lying in bed, as shown in FIG. 8.

Figure 9:
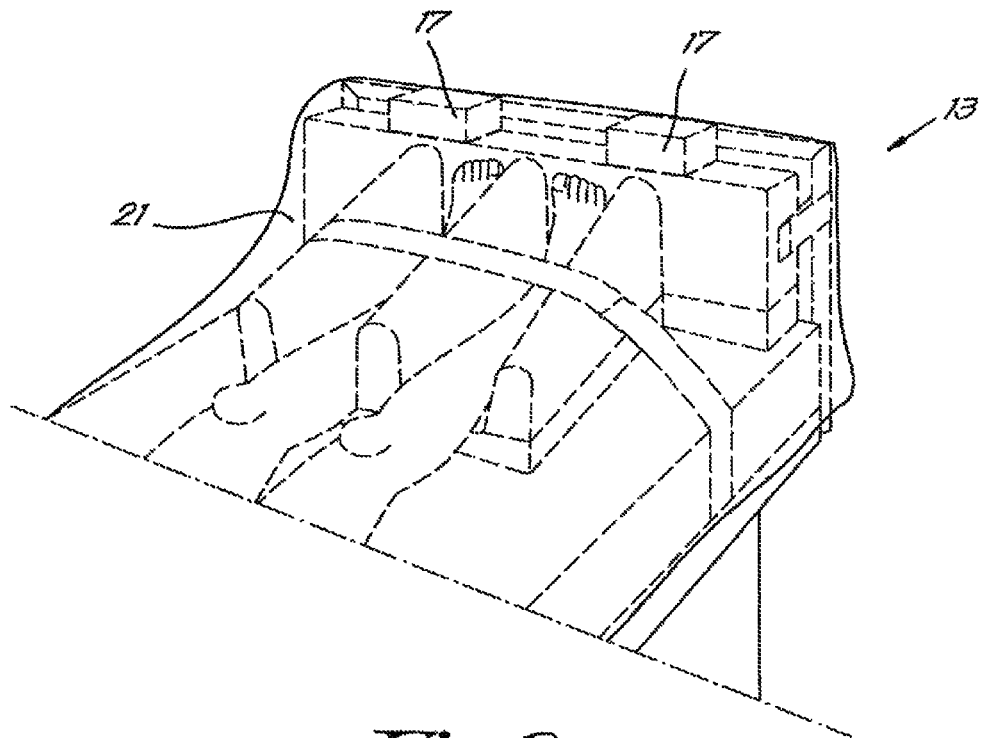
FIG. 9 is a view as in FIG. 3 but with the application of the bed covers.

FIG. 9 illustrates how the bed cover 21 can be placed over the foot support 13 without exerting pressure on the feet of the patient, while nevertheless adequately covering the feet to keep the feet warm.

Figure 10:
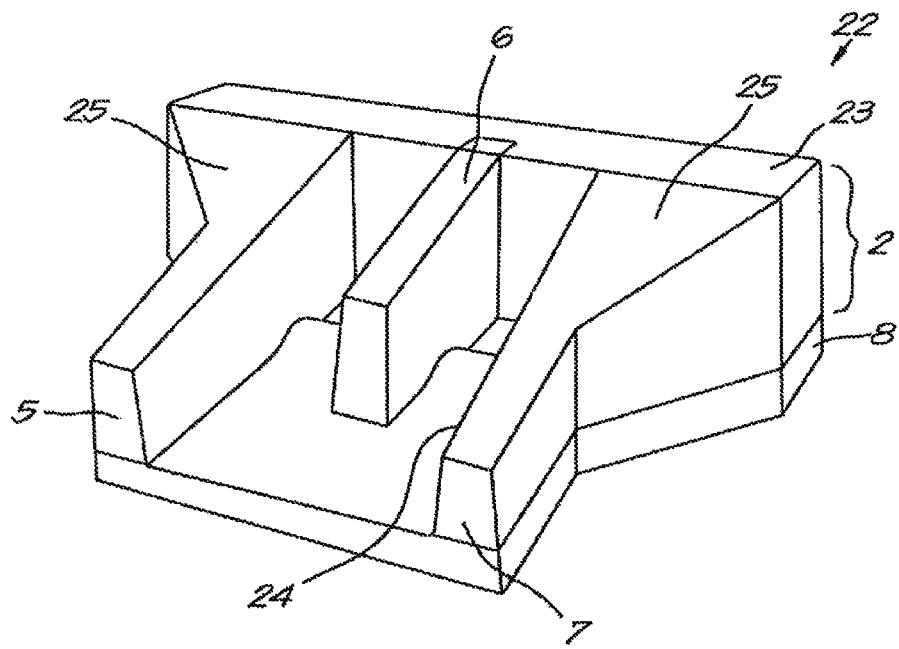
FIG. 10 shows an alternative embodiment of the invention.

An alternative embodiment 22 is presented in FIG. 10, whereby the beam shaped cushion 23 slopes down 24 towards the upper legs, and whereby lateral pushing aside is prevented by solid triangular supports 25 that lean on either side against the outer transverse supports 5,7 along the legs.

Figure 11:
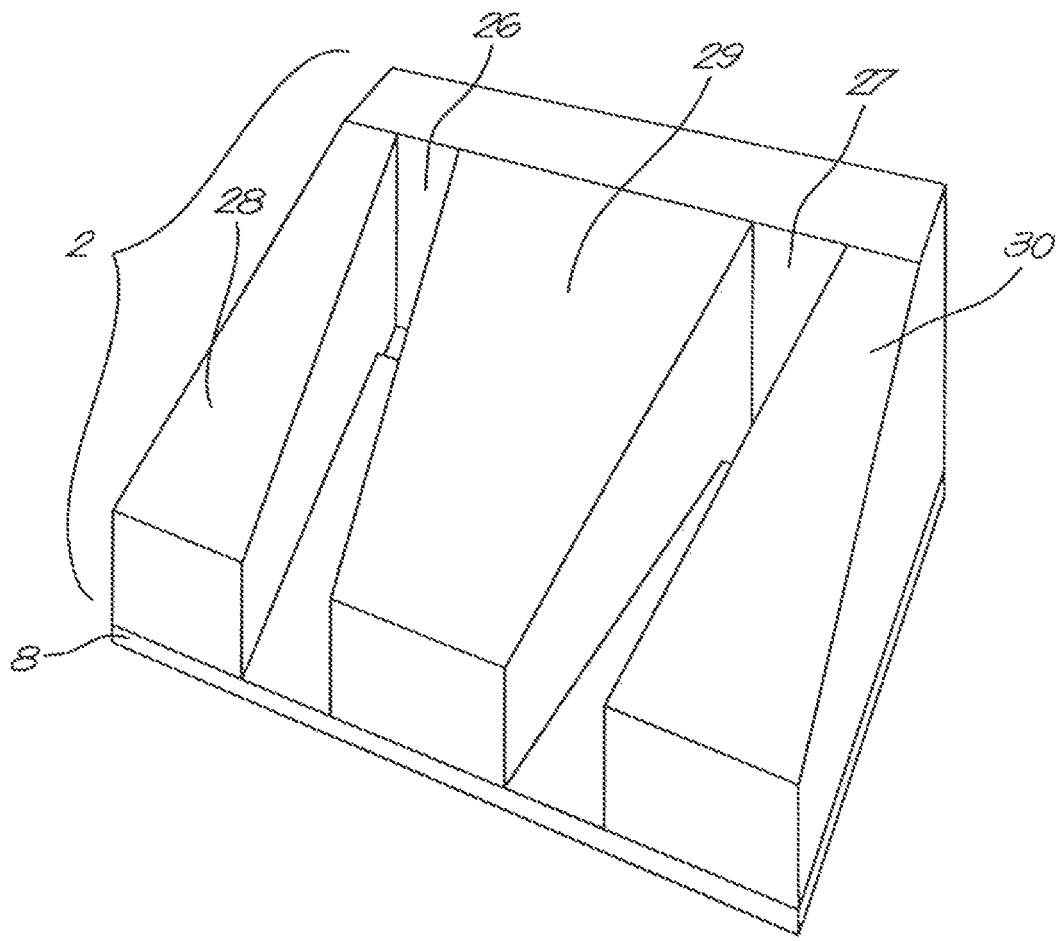
FIG. 11 shows a variant of FIG. 10 suitable for legs in the straddle position.

FIG. 11 shows a variant embodiment of the slots in which both legs of the patient are laid. In this variant, the legs are in a slight straddle position, as is desired for the repair after a hip fracture or hip operation. Here too the walls of the slots 26,27 are supported by solid transverse supports 28,29,30 to provide sideways support to the lower legs.

It goes without saying that such an orthopaedic foot support can be constructed in all types of sizes, materials and colours.

It is thus conceivable that base inserts 14 or bases 8 with cambers 10 can be selected from an array of different preformed sizes depending on the dimensions of the patient.

It is also conceivable that the stiff cushion 3 of the orthopaedic foot support can be constructed in different sizes, for example to provide a suitable size for adults and children, or for use in different bed sizes, whereby the top piece 2 can be attached or otherwise to the base 8 by means of attachments, zippers, hinges, buckles or other means of attachment.

Thus the base 8 with cambers can also be constructed with suitable edges, that can be slid in slots in the top piece or vice versa.

The present invention is by no means limited to the embodiments described as an example and shown in the drawings, but an orthopaedic foot support with base and removable top piece according to the invention can be realised in all kinds of variants, without departing from the scope of the invention.

The invention claimed is:

1. Orthopaedic foot support to support long-term bedridden patients, characterised in that the foot support comprises a preformed support of a top piece and a bottom piece, wherein the top piece consists of a stiff cushion with an erect wall and transverse supports connected to it for the lateral support of the lower legs, and the bottom piece consists of a base on which the lower legs can rest and whereby the base has a pair of cambers to support the lower legs, and whereby the base can be exchanged by a base with different cambers suitable for another leg dimension, and whereby the top piece can be removed to gain access to the legs of the patient who remains lying on the base, without having to move this base or the legs, and whereby the base and the erect wall of the top piece form a right angle or practically form a right angle so that the feet form a right angle or practically form a right angle with respect to the lower leg.

2. Orthopaedic foot support according to claim 1, characterised in that between the camber to support the lower leg and the upright wall of the top piece there is a hollow in the base and the upright wall such that the heel is located floating above the underlying base.

3. Orthopaedic foot support according to claim 1, characterised in that the top piece can be detached from the base to remove it and it can be secured after being put back on the base.

4. Orthopaedic foot support according to claim 3, characterised in that the top piece can be secured to the base with a hinge so that the top piece can be turned upwards to release the legs.

5. Orthopaedic foot support according to claim 3, characterised in that the top piece can be secured to the base by means of buckles or fasteners.

6. Orthopaedic foot support according to claim 3, characterised in that the top piece and the base can be secured to one another by sliding them together, and can be slid apart to remove the top piece.

7. Orthopaedic foot support according to claim 1, characterised in that the pair of cambers on the base is made from a material that automatically takes on the shape of the lower leg of the patient, such as a viscoelastic foam or a gel pad.

8. Orthopaedic foot support according to claim 1, characterised in that the edge of the base that is the closest to the back of the knee of the supported legs, has a height between 1 and 3 cm in order not to load the knee joint.

9. Orthopaedic foot support according to claim 1, characterised in that the base is no larger than the movable surface of a positionable hospital bed on which the lower legs rest.

10. Orthopaedic foot support according to claim 1, characterised in that the central support of the transverse supports, that keeps the two legs separate, can be detached to enable a sideways position for the patient.

11. Orthopaedic foot support according to claim 1, characterised in that the base and/or the top piece is covered on the underside with an anti-slip material, in order to prevent it sliding away when the support surface is on a slope.

12. Orthopaedic foot support according to claim 1, characterised in that the top piece and/or the base are made from a hard foam, such as polyether or polyurethane or a medical cold foam.

13. Orthopaedic foot support according to claim 12, characterised in that the hard foam consists of a mix of different foam types with possible different densities.

14. Orthopaedic foot support according to claim 12, characterised in that the hard foam is of a fire-retardant type.

15. Orthopaedic foot support according to claim 12, characterised in that the hard foam is an antibacterial and/or antiviral medical foam.

16. Orthopaedic foot support according to claim 12, characterised in that the hard foam core is covered with a softer material to improve the lying comfort of the patient.

17. Orthopaedic foot support according to claim 16, characterised in that the covering of the hard foam core is constructed in the form of a liner or coating.

18. Orthopaedic foot support according to claim 1, characterised in that the foot support consists of or is covered with a material that has properties to prevent bedsores.

19. Orthopaedic foot support according to claim 1, characterised in that the foot support is covered with a material that has antibacterial, antiviral and/or antifungal properties.

20. Orthopaedic foot support according to claim 1, characterised in that the foot support consists of or is covered with a material that can be washed or sterilised at 95° C.

21. Orthopaedic foot support according to claim 1, characterised in that the cambers in the base are formed by inserts chosen from a range of preformed inserts with cambers, according to the physiognomy of the lower leg and foot of the patient.

22. Orthopaedic foot support according to claim 1, characterised in that the top piece and/or base are equipped with securing means to secure them in place at the foot end of the bed.

23. Orthopaedic foot support according to claim 1, characterised in that height of the stiff upright cushion of the top piece is such that the patient can at most stretch out his toes above the stiff upright cushion.

24. Orthopaedic foot support according to claim 1, characterised in that the stiff upright cushion of the top piece has one or more extension pieces that ensure that the bed covers over the foot support do not come into contact with the feet of the patient.

25. Orthopaedic foot support according to claim 1, characterised in that a band at the level of the lower legs is attached around the cushion.

26. Orthopaedic foot support according to claim 1, characterised in that the three transverse supports include a central support that is intended to be placed between the legs of the patient in order to ensure a straddle position of the legs, and the other two supports are side supports on either side of the legs.

27. Orthopaedic foot support according to claim 1, characterised in that the transverse supports slope downwards in their longitudinal direction from the upright cushion to the edge of the base that is closest to the backs of the knees, in order to keep the upper legs warm with the bed covers.

* * * * *